United States Patent
Xu et al.

(10) Patent No.: US 12,158,405 B2
(45) Date of Patent: Dec. 3, 2024

(54) TBM-MOUNTED SYSTEM AND METHOD FOR QUICKLY PREDICTING COMPRESSIVE STRENGTH OF ROCKS BASED ON ROCK MINERAL COMPOSITION AND FABRIC CHARACTERISTICS

(71) Applicant: SHANDONG UNIVERSITY, Shandong (CN)

(72) Inventors: Zhenhao Xu, Jinan (CN); Huihui Xie, Jinan (CN); Shucai Li, Jinan (CN); Peng Lin, Jinan (CN); Xin Huang, Jinan (CN); Zhaoyang Wang, Jinan (CN); Dongdong Pan, Jinan (CN); Youbo Liu, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 323 days.

(21) Appl. No.: 17/777,801

(22) PCT Filed: Jan. 21, 2020

(86) PCT No.: PCT/CN2020/073614
§ 371 (c)(1),
(2) Date: May 18, 2022

(87) PCT Pub. No.: WO2021/142861
PCT Pub. Date: Jul. 22, 2021

(65) Prior Publication Data
US 2022/0412867 A1    Dec. 29, 2022

(30) Foreign Application Priority Data
Jan. 15, 2020    (CN) .......................... 202010043660.3

(51) Int. Cl.
*G01N 15/02*    (2024.01)
*G01N 15/0227*    (2024.01)
(Continued)

(52) U.S. Cl.
CPC ................. *G01N 15/0227* (2013.01)

(58) Field of Classification Search
CPC .... G01N 15/00; G01N 15/02; G01N 15/0227; G01N 29/07; G01N 33/24;
(Continued)

(56) References Cited

U.S. PATENT DOCUMENTS

2011/0259646 A1    10/2011    Hall et al.

FOREIGN PATENT DOCUMENTS

| CN | 109186480 A | * | 1/2019 | ............ G01B 11/16 |
| CN | 109374456 A |   | 2/2019 | |

(Continued)

OTHER PUBLICATIONS

Machine Translation of CN-109186480-A (Year: 2019).*
(Continued)

*Primary Examiner* — Nguyen Q. Ha
(74) *Attorney, Agent, or Firm* — Oliff PLC (57) ABSTRACT

A TBM-mounted system and method for quickly predicting compressive strength of rocks based on rock mineral composition and fabric characteristics. The system is mounted on gripper shoe's side surface of an open-type TBM, and includes a protective device, hydraulic device, servo motor, detection device, control system and a data comprehensive analysis platform. The hydraulic device is mounted on the protective device's side wall, for controlling movement of detection device horizontally. The servo motor controls rotation of detection device. The detection device collects a variety of geological parameters of target surrounding rock affecting compressive strength of rock and providing basic data for compressive strength prediction of rock. The control system controls work of hydraulic device, servo motor and each detection device. The data comprehensive analysis platform is connected to each detection instrument, receives
(Continued)

geological parameters collected, processes and analyzes each parameter, and gives a prediction of compressive strength of rock.

18 Claims, 3 Drawing Sheets

(51) Int. Cl.
*G01N 29/07* (2006.01)
*G01N 33/24* (2006.01)

(58) Field of Classification Search
CPC ..... G01N 2291/0232; G01N 2291/028; G01N 2291/02827
See application file for complete search history.

(56) References Cited

FOREIGN PATENT DOCUMENTS

| | | | |
|---|---|---|---|
| CN | 109612943 A | 4/2019 | |
| CN | 109668791 A | 4/2019 | |
| CN | 109669424 A | 4/2019 | |
| CN | 110672356 A | 1/2020 | |
| JP | 2002168840 A | * 6/2002 | ............. G01N 29/07 |

OTHER PUBLICATIONS

Machine Translation of JP-2002168840-A (Year: 2002).*
Sep. 30, 2020 International Search Report issued in International Patent Application No. PCT/CN2020/073614.
Sep. 30, 2020 Written Opinion issued in International Patent Application No. PCT/CN2020/073614.

* cited by examiner

TBM-MOUNTED SYSTEM AND METHOD FOR QUICKLY PREDICTING COMPRESSIVE STRENGTH OF ROCKS BASED ON ROCK MINERAL COMPOSITION AND FABRIC CHARACTERISTICS

TECHNICAL FIELD

The present disclosure belongs to the field of rock and soil mechanical property testing, and particularly relates to a TBM-mounted system and method for quickly predicting compressive strength of rocks based on rock mineral composition and fabric characteristics.

BACKGROUND

The description in this section merely provides background information related to the present disclosure and does not necessarily constitute the related art.

The uniaxial compressive strength of rock is the main index reflecting damage to the rock under the action of external force. It is one of the most basic mechanical parameters in underground engineering and engineering investigation. It is widely used in rock foundation design, tunnel surrounding rock classification, rock mass quality grading, support parameter design optimization, construction method selection and informatization construction.

At present, there are two main conventional methods to acquire the uniaxial compressive strength of rock. One is to directly measure the uniaxial compressive strength of rock by using a uniaxial compression testing machine, and the other is to calculate the uniaxial compressive strength of rock through point load tests. The uniaxial compression testing machine is used to directly test a rock sample in a laboratory, and testing needs to meet corresponding standards of the International Society of Rock Mechanics. Therefore, this testing method subject to many restrictions, for example, the rock test sample is required to be complete and cannot contain joint fissures, sampling and sample processing are complicated, and the like. Consequently, it is difficult to obtain qualified high-quality rock cores in highly broken, weak and weathered rock masses. In addition, the uniaxial compression testing machine is used to directly determine the uniaxial compressive strength of rock, which also has limitations such as long test period, high cost, and inability to test the disturbed surrounding rock after excavation in real time. The method for calculating the uniaxial compressive strength of rock through point load tests has the advantages of rapid on-site testing, low requirements for the shape of the test sample, and the like, but using this method to calculate the uniaxial compressive strength of rock also has the problems that the test results of a point load instrument are large in discrete type and the calculating results are low in accuracy. Therefore, there is an urgent need to develop an indirect method and system which is economical, easy to implement, and high in test result accuracy to predict the uniaxial compressive strength of rock.

SUMMARY

In order to solve the above problems, the present disclosure provides a TBM-mounted system and method for quickly predicting compressive strength of rocks based on rock mineral composition and fabric characteristics. The present disclosure indirectly predicts the uniaxial compressive strength of rock more quickly and accurately by testing and quantitatively analyzing the mineral composition and fabric characteristics playing a decisive role in the uniaxial compressive strength of rock.

According to some embodiments, the present disclosure adopts the following technical solutions:

A system for quickly predicting compressive strength of rocks based on rock mineral composition and fabric characteristics is mounted on a side surface of a gripper shoe of an open-type TBM, and includes a protective device, a hydraulic device, a servo motor, a detection device, a control system and a data comprehensive analysis platform.

The protective device includes a base, a side wall and a ceiling, the side wall is arranged on the base, a top end of the side wall is provided with the ceiling, and the protective device is used to provide support for other parts of the system and prevent damage by block falling, water seepage, and the like of tunnel walls to other parts of the system.

The hydraulic device is mounted on the side wall of the protective device, and includes a hydraulic arm, a hydraulic pump and a hydraulic valve, for controlling movement of the detection device in a horizontal direction.

The servo motor is used to control rotation of the detection device in the system, so that different parts of the same target surrounding rock can be detected, thereby ensuring the scientificity and effectiveness of collected data.

The detection device includes a variety of detection instruments for collecting a variety of geological parameters affecting the compressive strength of rock from the target surrounding rock, and providing basic data for predicting the compressive strength of rock.

The control system is used to control work of the hydraulic device, the servo motor and each detection device.

The data comprehensive analysis platform is connected to each detection instrument in the detection device via a cable, receives geological parameters collected by each of the above instruments, processes and analyzes each parameter, and finally gives a prediction result of the compressive strength of rock.

As a further technical solution, the base of the protective device is made of a stainless steel plate, and is in a rectangular shape, the side wall is vertically welded above the base, and the ceiling is also made of a stainless steel plate.

As a further technical solution, the detection device consists of a cross frame, a non-metallic ultrasonic detector, an element analyzer and a rock image collector.

As a further technical solution, the cross frame has four equal-length wings, and two transducers of the non-metallic ultrasonic detector, the rock image collector and the element analyzer are respectively mounted at wing ends thereof. Cooperating with the rotation of the servo motor, the four equal-length wings of the cross frame ensure that the non-metallic ultrasonic detector, the image collector and the element analyzer can carry out data collection work on different parts of the target surrounding rock.

As a further technical solution, the non-metallic ultrasonic detector is used to acquire an acoustic wave velocity $V_p$ of an acoustic wave propagating in the rock. The non-metallic ultrasonic detector includes a host system, cross beams, energy converters, springs and washer pressure sensors. The host system is fixedly mounted in the middle of the cross frame, the host system has one cross beam on each of two sides, and the washer pressure sensors, the springs and the energy converters are symmetrically mounted at two ends of the cross beam. The total length of the washer pressure sensor, the transducer and spring is longer than the length of the element analyzer and length of the image collector by 10 cm or more so as to ensure that the transducer contacts with the surrounding rock first when the detection device extends out for detection. When the spring is compressed after the transducer contacts with the surrounding rock, the control system can control the hydraulic device to stop working after a pressure received by the washer pressure sensor reaches a certain level.

As a further technical solution, the image collector is a digital magnifier, and the magnifier can magnify a target image by 25-600 times, and has the functions of photographing, camera shooting and auxiliary measuring, and is used to collect images of the target surrounding rock and transmit the images into the data comprehensive analysis platform.

As a further technical solution, the element analyzer is a portable energy dispersive X-ray fluorescence analyzer, which is mainly consists of a power supply device, an excitation source, a detector, a pre-amplifier, a main amplifier, a multichannel pulse amplitude analyzer and a microcomputer system. The excitation source uses a low-power X-ray tube which emits X-rays to the target surrounding rock. The detector uses a proportional detector which detects the mineral composition and structure of the target surrounding rock. A signal detected by the detector is amplified by the pre-amplifier and the main amplifier and then sent to the multichannel pulse amplitude analyzer and a spectral analysis system for analysis.

As a further technical solution, the data comprehensive analysis platform is a computer mounted in a TBM master control room, and a grain size analysis system, a mineral composition analysis system and a uniaxial compressive strength prediction system developed based on the Windows system are mounted in the platform.

As a further technical solution, the grain size analysis system measures and calibrates a grain size of the rock in the collected rock image using a deep learning technique, and calculates a grain size parameter using a Fock-Ward formula $$M_z = \frac{\phi_{16} + \phi_{50} + \phi_{84}}{3},$$

wherein $M_z$ is an average grain diameter, and $\phi_i$ is a grain diameter corresponding to a grain content of i %.

As a further technical solution, the mineral composition analysis system is based on a software system developed by a programming language VC++, and the system converts rock element types and contents acquired by an element analysis system into mineral types and contents of rock using a CIPW standard mineral calculation method.

As a further technical solution, the uniaxial compressive strength prediction system receives information input from the grain size analysis system, the mineral composition analysis system and the non-metallic ultrasonic detector and performs compressive strength prediction on the target surrounding rock. The system uses a BP neural network intelligent inversion method to establish a uniaxial compressive strength prediction model.

As a further limitation, the uniaxial compressive strength prediction model established based on a BP neural network includes a training set and a prediction set. The training set is a database established in the previous period for carrying out grain size analysis, mineral composition analysis, longitudinal wave velocity analysis and standard compressive strength testing, and the prediction set is relevant parameters detected by the system in a TBM boring process.

A working method based on the system is provided, including the following steps:
in the TBM boring process, enabling a gripper shoe of a TBM to cling to surrounding rock of a tunnel so as to bear a reaction and a reaction torque transmitted during working of a TBM cutterhead system; at this time, starting a hydraulic pump, and controlling a hydraulic arm by a hydraulic control valve, so that a transducer of a non-metallic ultrasonic detector contacts with target surrounding rock, and probes of an image collector and an element analyzer are close to the target surrounding rock;
starting the non-metallic ultrasonic detector, the image collector and the element analyzer to work at the same time to respectively collect a longitudinal wave velocity, a rock image and element information of the target surrounding rock, and transmit them into a data comprehensive analysis platform;
starting a servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;
repeating the step of "starting a servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;
performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and
receiving information input from the grain size analysis system, the mineral composition analysis system and the non-metallic ultrasonic detector by the uniaxial compressive strength prediction system and performing compressive strength prediction on the target surrounding rock.

Compared with the prior art, the present disclosure has the following beneficial effects:

Through the skillful design of the present disclosure, each tester in the detection device can perform detection on the same part of the target surrounding rock by using the servo motor and the cross frame, so as to make a detection result more accurate.

According to the present disclosure, the mineral composition and fabric characteristics playing a decisive role in the uniaxial compressive strength of rock are tested and quantitatively analyzed, and the longitudinal wave velocity, grain size and mineral types and contents of the rock are used to indirectly predict the uniaxial compressive strength of rock accurately.

Mounted on the TBM, the present disclosure can collect mineral composition and fabric information about the target surrounding rock in the TBM boring process, and analyze the compressive strength of the surrounding rock in the TBM boring process in real time by using the grain size analysis system, the mineral analysis system and the uniaxial compressive strength prediction system developed in the data comprehensive analysis platform.

BRIEF DESCRIPTION OF THE DRAWINGS

The accompanying drawings constituting a part of the present disclosure are used for providing further understanding for the present disclosure. Exemplary embodiments of the present disclosure and descriptions thereof are used for explaining the present disclosure and do not constitute any inappropriate limitation to the present disclosure.

In the drawings: 1. TBM gripper shoe; 2. Base; 3. Side wall; 4. Ceiling; 5. Hydraulic arm; 6. Hydraulic pump; 7. Hydraulic valve; 8. Servo motor; 9. Detection device; 10. Control system; 11. Data comprehensive analysis platform; 12. TBM master control room; 9-1. Cross frame; 9-2. Host system; 9-3. Cross beam; 9-4. Washer pressure sensor; 9-5. Spring; 9-6. Transducer; 9-7. Image collector; and 9-8. Element analyzer.

DETAILED DESCRIPTION

The present disclosure is further described below with reference to the accompanying drawings and embodiments.

Embodiment 1

Figure 1:
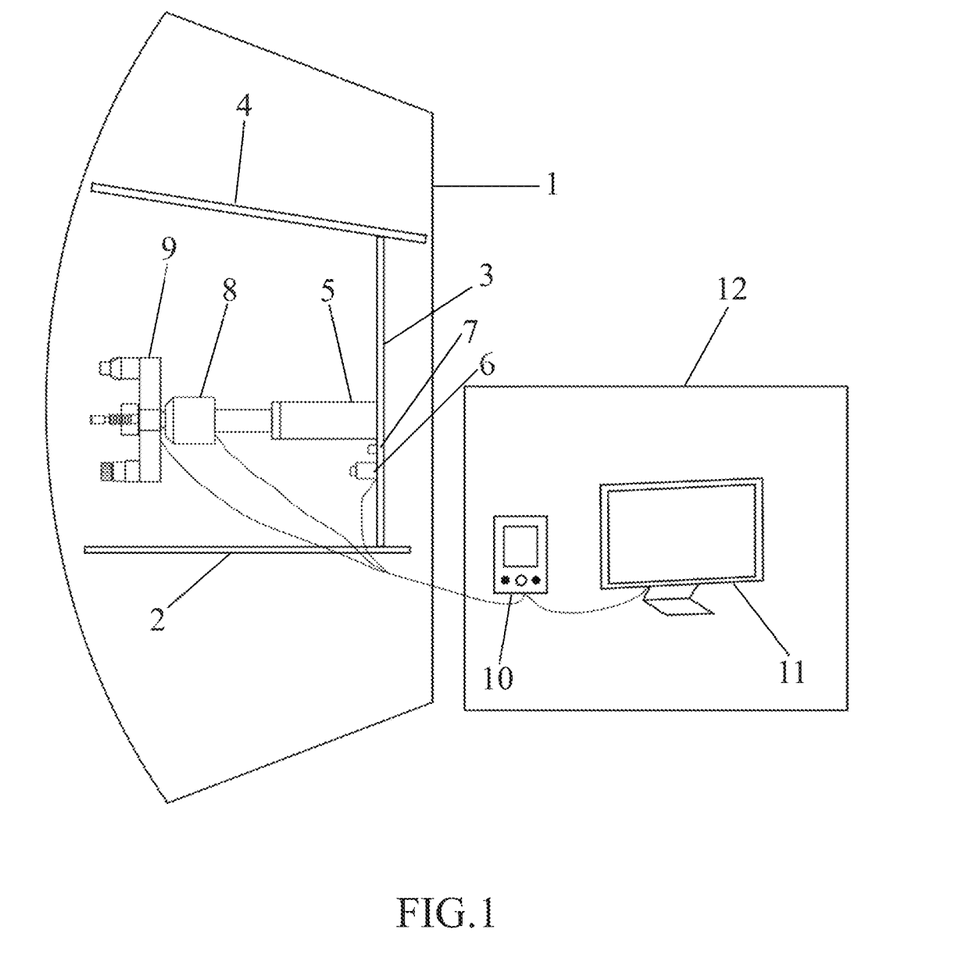
FIG. 1 is a structural schematic diagram of the present disclosure.

A system and method for quickly predicting compressive strength of rocks based on rock mineral composition and fabric characteristics disclosed in this embodiment, as shown in FIG. 1, includes a base 2, a side wall 3, a ceiling 4, a hydraulic arm 5, a servo motor 8, a detection device 9, a control system 10, and a data comprehensive analysis platform 11.

The base 2, the side wall 3 and the ceiling 4 jointly constitute the protective device of a sampling device, which can not only prevent the rockfall, water seepage, and the like of a tunnel vault from damaging instrument parts therein, but also provide support for other parts of the system. Preferably, the base 2 is made of a stainless steel plate and is in a rectangular shape. The side wall 3 is vertically welded above the base 2. The ceiling 4 is welded to a top of the side wall 3. The ceiling 4 is also made of a stainless steel plate.

The hydraulic device is mounted on the side wall 3, and includes the hydraulic arm 5, a hydraulic pump 6 and a hydraulic valve 7, for controlling movement of the detection device in a horizontal direction.

The servo motor 8 is used to control rotation of the detection device 9 in the system, so that different parts of the same target surrounding rock can be detected, thereby ensuring the scientificity and effectiveness of collected data.

The servo motor 8 is fixed to an end of the hydraulic arm 5. The hydraulic arm 5 can drive the servo motor 8 and the detection device 9 to move in the horizontal direction, so that the detection device 9 is close to or away from a rock wall.

The detection device 9 includes a variety of detection instruments, for collecting a variety of geological parameters affecting the compressive strength of rock from the target surrounding rock and providing basic data for predicting the compressive strength of rock.

The control system 10 is used to control work of the hydraulic device, the servo motor and each detection device.

The data comprehensive analysis platform 11 is connected to each detection instrument in the detection device 9 via a cable, receives geological parameters collected by each of the above instruments, processes and analyzes each parameter, and finally gives a prediction result of the compressive strength of rock.

Figure 2:
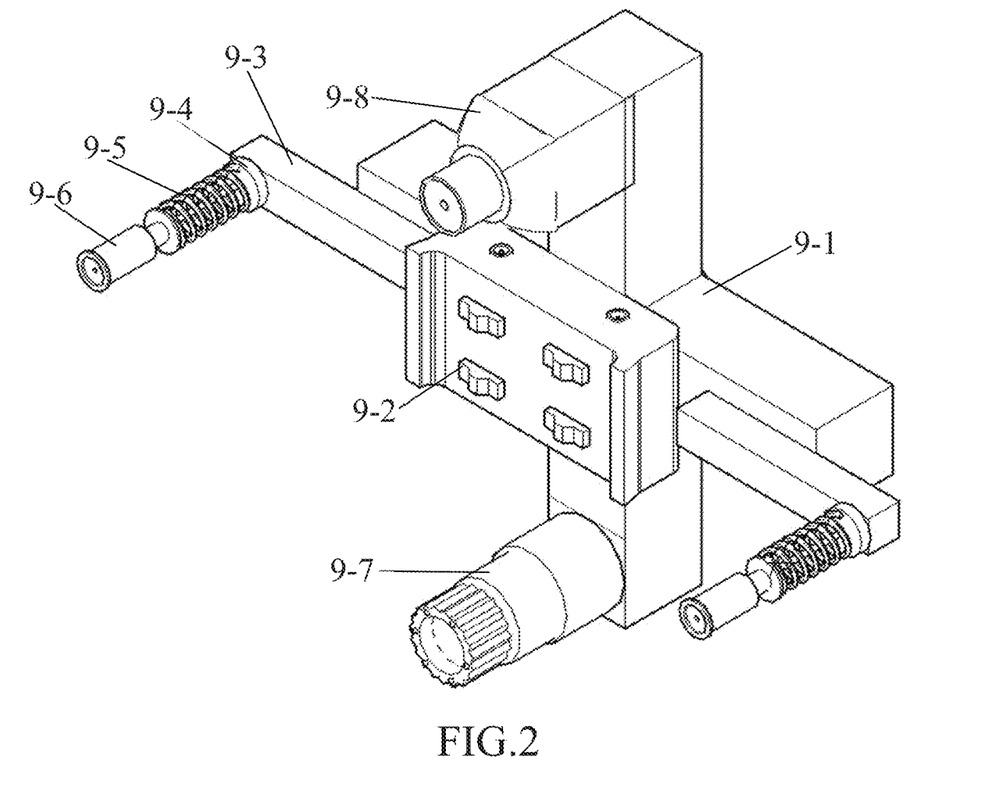
FIG. 2 is a structural diagram of a detection device of the present disclosure.

As shown in FIG. 2, the detection device consists of a cross frame 9-1, various parts of a non-metallic ultrasonic detector, a rock image collector 9-7 and an element analyzer 9-8.

Further, the cross frame 9-1 has four equal-length wings, and two transducers of the non-metallic ultrasonic detector, the rock image collector and the element analyzer are respectively mounted at wing ends thereof. Cooperating with the rotation of the servo motor, the four equal-length wings of the cross frame ensure that the non-metallic ultrasonic detector, the image collector and the element analyzer can carry out data collection work on different parts of the target surrounding rock.

Further, the non-metallic ultrasonic detector includes a host system 9-2, cross beams 9-3, washer pressure sensors 9-4, springs 9-5 and the transducers 9-6. The host system 9-2 is fixedly mounted in the middle of the cross frame, the host system has one cross beam 9-3 on each of two sides, and the two cross beams 9-3 are fixed to two symmetrically arranged wings of the cross frame 9-1. In this embodiment, the two cross beams 9-3 are fixed to horizontally arranged wings. The washer pressure sensor 9-4, the spring 9-5 and the transducer 9-6 are mounted on each cross beam. Further preferably, the washer pressure sensors 9-4, the springs 9-5 and the transducers 9-6 on the two cross beams are mounted symmetrically with respect to a center line of the cross frame 9-1. The washer pressure sensor 9-4 is fixed to the cross beam 9-3, one end of the spring 9-5 is connected to the washer pressure sensor 9-4, and the other end of the spring 9-5 is connected to the transducer 9-6.

Further, the image collector 9-7 is a digital magnifier. The magnifier can magnify a target image by 25-600 times, and has the functions of photographing, camera shooting and auxiliary measuring, for collecting images of the target surrounding rock and transmitting the images into the data comprehensive analysis platform. It is also fixed to the cross frame, and in this embodiment, the image collector 9-7 is located below the host system 9-2.

Figure 3:
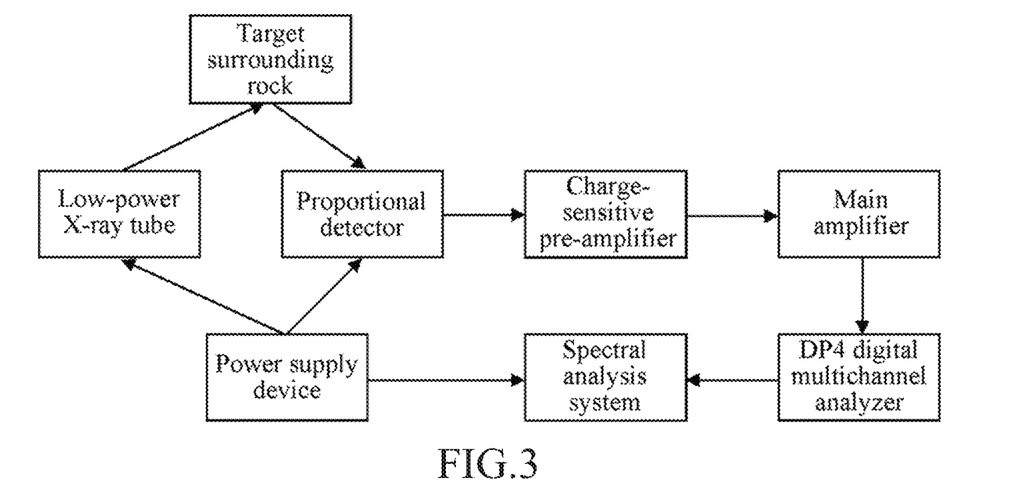
FIG. 3 is a structural block diagram of a portable energy dispersive X-ray fluorescence analyzer of the present disclosure.

Further, the element analyzer 9-8 is a portable energy dispersive X-ray fluorescence analyzer, as shown in FIG. 3. It mainly consists of a power supply device, an excitation source, a detector, a pre-amplifier, a main amplifier, a multichannel pulse amplitude analyzer and a spectral analysis system. The excitation source uses a low-power X-ray tube which emits X-rays to the target surrounding rock. The detector uses a proportional detector which detects the mineral composition and structure of the target surrounding rock. A signal detected by the detector is amplified by the pre-amplifier (corresponding to a charge-sensitive pre-amplifier in the figure) and the main amplifier and then sent to the multichannel pulse amplitude analyzer (corresponding to a DP4 digital multichannel analyzer in the figure) and the spectral analysis system for analysis. The elemental analyzer 9-8 is also fixed to the cross frame, and in this embodiment, the elemental analyzer 9-8 is located above the host system 9-2.

Specifically, the power supply device can provide high and low voltage power supplies, and the excitation source is the low-power X-ray tube. The proportional detector which has better detection efficiency and energy resolution, and is lower in environmental requirement, and suitable for on-site observation is selected as the detector. The pre-amplifier is the charge-sensitive preamplifier with good low noise performance. In order to optimize the energy resolution of an energy dispersive system, a main amplifying circuit is designed to be composed of a first-level differential circuit and a second-level integral circuit, and at the same time, various levels are separated by a buffer amplifier. The multichannel pulse amplitude analyzer uses the DP4 digital multichannel analyzer produced by AMPTEK Company in the United States. A software system is existing spectral analysis software developed based on the Window operating system, which can display and analyze spectral line data collected by the detector and transmit an analysis result. The portable energy dispersive X-ray fluorescence analyzer can give element types and contents in the target surrounding rock, and transmit the result into the data comprehensive analysis platform.

The control system 10 is used to control work of the hydraulic device, the servo motor and each detection device.

The data comprehensive analysis platform 11 is connected to each detection instrument in the detection device via a cable, receives geological parameters collected by each of the above instruments, processes and analyzes each parameter, and finally gives a prediction result of the compressive strength of rock.

Further, the data comprehensive analysis platform 11 is a computer mounted in a TBM master control room 12, and a grain size analysis system, a mineral composition analysis system and a uniaxial compressive strength prediction system developed based on the Windows system are mounted in the platform.

Specifically, the grain size analysis system measures and calibrates a grain size of the rock in the collected rock image using a deep learning technique, and calculates a grain size parameter using a Fock-Ward formula $$M_z = \frac{\phi_{16} + \phi_{50} + \phi_{84}}{3},$$

wherein $M_z$ is an average grain diameter, and $\phi_i$ is a grain diameter corresponding to a grain content of i %.

Specifically, the mineral composition analysis system is based on a software system developed by a programming language VC++, and the system converts rock element types and contents acquired by an element analysis system into rock mineral types and contents using a CIPW standard mineral calculation method. A specific implementation method is: firstly, a mass percentage of each element acquired by XRF is converted into a mass percentage of oxide, and then is converted into the number of molecules, secondly, the number of molecules of MnO and FeO is combined into the number of molecules of FeO; later, a small amount of mineral components such as $P_2O_5$, $TiO_2$ and $Cr_2O_3$ are combined into accessory minerals; and finally, main mineral components are combined into essential minerals by determining rock types. The small amount of mineral components include $P_2O_5$, $TiO_2$, $Cr_2O_3$ and the like. The rock types include a normal type, an aluminum supersaturated type, and an alkali supersaturated type. The main mineral components include $SiO_2$, $K_2O$, $Na_2O$, $Al_2O_3$, CaO, MgO, FeO(FeO+MnO), $Fe_2O_3$, and the like.

Specifically, the uniaxial compressive strength prediction system receives information input from the grain size analysis system, the mineral composition analysis system and the non-metallic ultrasonic detector and performs compressive strength prediction on the target surrounding rock. The system uses a BP neural network intelligent inversion method to establish a uniaxial compressive strength prediction model. A specific method is: a wave velocity value, an average grain size, mineral types and contents of the target surrounding rock are selected as a network input layer, and the compressive strength of rock is used as an output layer; a transfer function of the input layer uses logsig, a transfer function of the output layer uses tansi, the number of hidden layers is 1, and the number of neurons is estimated according to the following formula: $N=\sqrt{i+j}+a$, wherein N is the number of neurons in the hidden layer, i is the number of neurons in the input layer, j is the number of neurons in the output layer, and a is a constant, and may be (1, 10); a final value of N needs to be debugged repeatedly, and a value at which a network training process is relatively stable, the number of iterations is smallest, an iteration value is closest to a target value, and the performance is optimal is selected.

Specifically, the uniaxial compressive strength prediction model established based on a BP neural network includes a training set and a prediction set. The training set is a database established in the previous period for carrying out grain size analysis, mineral composition analysis, longitudinal wave velocity analysis and standard compressive strength testing, and the prediction set is relevant parameters detected by the system in a TBM boring process.

Embodiment 2

Figure 4:
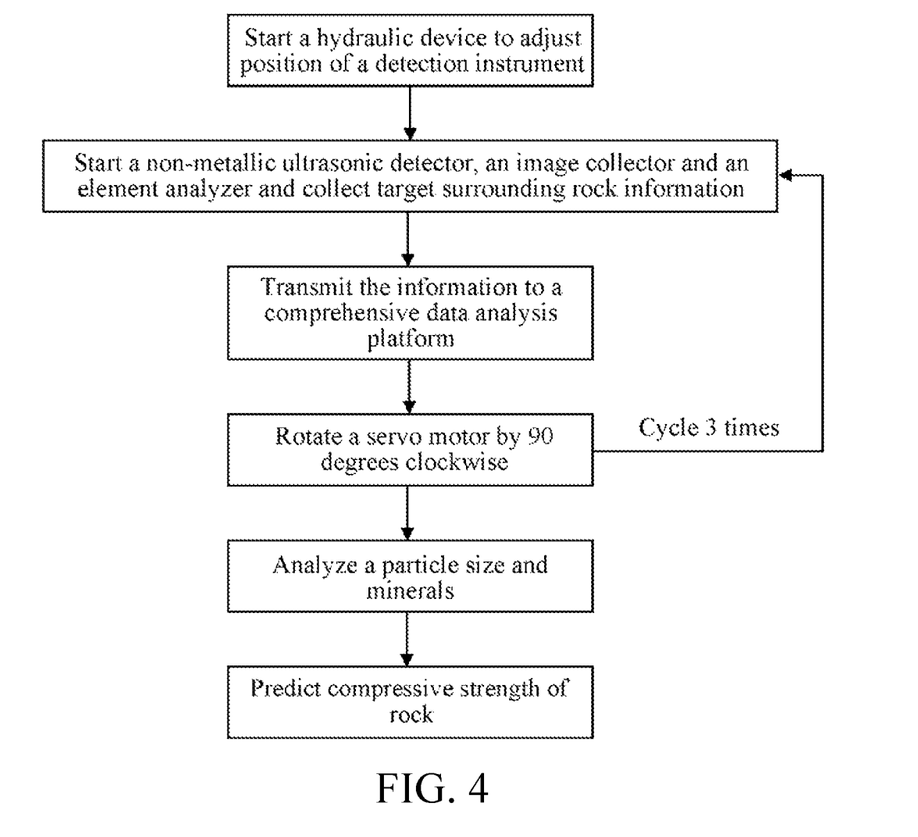
FIG. 4 is a work flow diagram of the present disclosure.

This embodiment provides a using method of a TBM-mounted system for quickly predicting compressive strength of rocks based on rock mineral composition and fabric characteristics based on Embodiment 1, as shown in FIG. 4, including:

step A: in the TBM boring process, a gripper shoe 1 of a TBM will cling to surrounding rock of a tunnel so as to bear a reaction and reaction torque transmitted during working of a TBM cutterhead system; at this time, a hydraulic pump 6 is started, and a hydraulic arm 5 is controlled by a hydraulic valve 7, so that a transducer 9-6 of a non-metallic ultrasonic detector contacts with target surrounding rock, and probes of an image collector 9-7 and an element analyzer 9-8 are close to the target surrounding rock;

step B: the non-metallic ultrasonic detector, the image collector and the element analyzer start to work at the same time to respectively collect a longitudinal wave velocity, a rock image and element information of the target surrounding rock, and transmit them into a data comprehensive analysis platform 11;

step C: a servo motor 6 is started and stops working after rotating by 90 degrees clockwise, the non-metallic ultrasonic detector, the image collector and the element analyzer start working again, and transmit the target surrounding rock information collected respectively into the data comprehensive analysis platform again;

step D: work in step C is repeated twice;

step E: a grain size analysis system in the data comprehensive analysis platform 11 performs grain size analysis on images collected many times by the image collector 9-7, and gives an average value of the grain size analysis, at the same time, a mineral composition analysis system takes an average value of element information collected many times by the element analyzer 9-8 and converts it into mineral types and contents, and then the above analysis results are transmitted to a uniaxial compressive strength prediction system; and step F: the uniaxial compressive strength prediction system receives information input from the grain size analysis system, the mineral composition analysis system and the non-metallic ultrasonic detector and performs compressive strength prediction on the target surrounding rock.

What is claimed is:

1. A TBM-mounted system for quickly predicting compressive strength of rocks based on rock mineral composition and fabric characteristics, mounted on a side surface of a gripper shoe of an open-type TBM, comprising a protective device, a hydraulic device, a servo motor, a detection device, a control system and a data comprehensive analysis platform, wherein:

the protective device comprises a base, a side wall and a ceiling, the side wall is vertically arranged on the base, and a top end of the side wall is provided with the ceiling; the hydraulic device is mounted on the side wall of the protective device, and comprises a hydraulic arm, a hydraulic pump and a hydraulic valve, for controlling movement of the detection device in a horizontal direction;

the servo motor is mounted at an end of the hydraulic arm, for controlling rotation of the detection device in the system, so that different parts of the same target surrounding rock can be detected, thereby ensuring the scientificity and effectiveness of collected data;

the detection device comprises a variety of detection instruments, for collecting a variety of geological parameters affecting the compressive strength of rock of the target surrounding rock and providing basic data for predicting the compressive strength of rock;

the control system is used to control work of the hydraulic device, the servo motor and each detection device;

the data comprehensive analysis platform is connected to each detection instrument in the detection device via a cable, receives the geological parameters collected by each of the above instruments, processes and analyzes each parameter, and finally gives a prediction result of the compressive strength of rock.

2. The TBM-mounted system for quickly predicting compressive strength of rocks based on rock mineral composition and fabric characteristics according to claim 1, wherein the detection device comprises a cross frame, a non-metallic ultrasonic detector, an element analyzer and a rock image collector; and the cross frame has four equal-length wings, and two transducers of the non-metallic ultrasonic detector, the rock image collector and the element analyzer are respectively mounted at wing ends thereof.

3. The TBM-mounted system for quickly predicting compressive strength of rocks based on rock mineral composition and fabric characteristics according to claim 2, wherein the non-metallic ultrasonic detector is used to acquire an acoustic wave velocity $V_p$ of an acoustic wave propagating in the rock, and comprises a host system, cross beams, the transducers, springs and washer pressure sensors, wherein the host system is fixedly mounted in the middle of the cross frame, the host system has one cross beam on each of two sides, and the washer pressure sensors, the springs and the transducers are symmetrically mounted at two ends of the cross beam; wherein the washer pressure sensor, the transducers and the springs are positioned higher than the image collector.

4. The TBM-mounted system for quickly predicting compressive strength of rocks based on rock mineral composition and fabric characteristics according to claim 2, wherein the image collector is a digital magnifier, and has the functions of photographing, camera shooting and auxiliary measuring, for collecting images of the target surrounding rock and transmitting the images into the data comprehensive analysis platform.

5. The TBM-mounted system for quickly predicting compressive strength of rocks based on rock mineral composition and fabric characteristics according to claim 2, wherein the element analyzer is a portable energy dispersive X-ray fluorescence analyzer, which comprises a power supply device, an excitation source, a detector, a pre-amplifier, a main amplifier, a multichannel pulse amplitude analyzer and a microcomputer system; wherein the excitation source uses a low-power X-ray tube which emits X-rays to the target surrounding rock, and the detector uses a proportional detector which detects the mineral composition and structure of the target surrounding rock; and a signal detected by the detector is amplified by the pre-amplifier and the main amplifier and then sent to the multichannel pulse amplitude analyzer and a spectral analysis system for analysis.

6. The TBM-mounted system for quickly predicting compressive strength of rocks based on rock mineral composition and fabric characteristics according to claim 2, wherein the data comprehensive analysis platform is a computer mounted in a TBM master control room, and a grain size analysis system, a mineral composition analysis system and a uniaxial compressive strength prediction system are mounted in the platform.

7. The TBM-mounted system for quickly predicting compressive strength of rocks based on rock mineral composition and fabric characteristics according to claim 6, wherein the grain size analysis system measures and calibrates a grain size of the rock in the collected rock image using a deep learning technique, and calculates a grain size parameter using a Fock-Ward formula $$M_z = \frac{\phi_{16} + \phi_{50} + \phi_{84}}{3},$$

wherein $M_z$ is an average grain diameter, and $\varphi_i$ is a grain diameter corresponding to a grain content of i %.

8. The TBM-mounted system for quickly predicting compressive strength of rocks based on rock mineral composition and fabric characteristics according to claim 6, wherein the mineral composition analysis system converts rock element types and contents acquired by an element analysis system into rock mineral types and contents using a CIPW standard mineral calculation method.

9. The TBM-mounted system for quickly predicting compressive strength of rocks based on rock mineral composition and fabric characteristics according to claim 6, wherein the uniaxial compressive strength prediction system receives information input from the grain size analysis system, the mineral composition analysis system and the non-metallic ultrasonic detector and performs compressive strength prediction on the target surrounding rock.

10. A working method of the system according to claim 1, comprising:
- in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that a transducer of a non-metallic ultrasonic detector contacts with target surrounding rock, and probes of an image collector and an element analyzer are close to the target surrounding rock;
- starting the non-metallic ultrasonic detector, the image collector and the element analyzer to work at the same time to respectively collect a longitudinal wave velocity, a rock image and element information of the target surrounding rock, and transmit them into the data comprehensive analysis platform;
- starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;
- repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;
- performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and
- receiving information input from the grain size analysis system, the mineral composition analysis system and the non-metallic ultrasonic detector by the uniaxial compressive strength prediction system and performing compressive strength prediction on the target surrounding rock.

11. A working method of the system according to claim 2, comprising:
- in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;
- starting the non-metallic ultrasonic detector, the image collector and the element analyzer to work at the same time to respectively collect a longitudinal wave velocity, a rock image and element information of the target surrounding rock, and transmit them into the data comprehensive analysis platform;
- starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;
- repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;
- performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and
- receiving information input from the grain size analysis system, the mineral composition analysis system and the non-metallic ultrasonic detector by the uniaxial compressive strength prediction system and performing compressive strength prediction on the target surrounding rock.

12. A working method of the system according to claim 3, comprising:
- in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;
- starting the non-metallic ultrasonic detector, the image collector and the element analyzer to work at the same time to respectively collect a longitudinal wave velocity, a rock image and element information of the target surrounding rock, and transmit them into the data comprehensive analysis platform;
- starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;
- repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;
- performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

13. A working method of the system according to claim 4, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

14. A working method of the system according to claim 5, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

15. A working method of the system according to claim 6, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic a hydraulic-pump, and controlling the hydraulic arm by the hydraulic control-valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

16. A working method of the system according to claim 7, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

17. A working method of the system according to claim 8, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling the hydraulic arm by the hydraulic valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

18. A working method of the system according to claim 9, comprising:

in a TBM boring process, enabling a gripper shoe of a TBM to cling to surrounding rock of a tunnel so as to bear a reaction and a reaction torque transmitted during working of a TBM cutterhead system; at this time, starting the hydraulic pump, and controlling a hydraulic arm by the hydraulic valve, so that the transducer of a non-metallic ultrasonic detector contacts with target surrounding rock, and probes of an image collector and an element analyzer are close to the target surrounding rock;

starting the non-metallic ultrasonic detector, the image collector and the element analyzer to work at the same time to respectively collect a longitudinal wave velocity, a rock image and element information of the target surrounding rock, and transmit them into the data comprehensive analysis platform;

starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again;

repeating the step of "starting the servo motor and stopping working after rotating by 90 degrees clockwise, and enabling the non-metallic ultrasonic detector, the image collector and the element analyzer to start to work again, and transmit the target surrounding rock information collected respectively into the data comprehensive analysis platform again" twice;

performing grain size analysis on images collected many times by the image collector by a grain size analysis system in the data comprehensive analysis platform, and giving an average value of the grain size analysis, at the same time, taking an average value of element information collected many times by the element analyzer by a mineral composition analysis system and converting it into mineral types and contents, and then transmitting the above analysis results to a uniaxial compressive strength prediction system; and receiving information input from the grain size analysis system, the mineral composition analysis system and the non-metallic ultrasonic detector by the uniaxial compressive strength prediction system and performing compressive strength prediction on the target surrounding rock.

* * * * *